United States Patent [19]

Holbrook et al.

[11] Patent Number: 5,105,032
[45] Date of Patent: Apr. 14, 1992

[54] VAPOR PHASE HYDROGENATION OF CARBON TETRACHLORIDE

[75] Inventors: Michael T. Holbrook, Baton Rouge, La.; A. Dale Harley, Midland, Mich.

[73] Assignee: The Dow Chemical Company, Midland, Mich.

[21] Appl. No.: 592,724

[22] Filed: Oct. 4, 1990

[51] Int. Cl.$^5$ .............. C07C 17/00; C07C 19/04; C07C 19/02
[52] U.S. Cl. .............. 570/101; 585/733; 502/339
[58] Field of Search .............. 570/101

[56] References Cited

U.S. PATENT DOCUMENTS

| | | | |
|---|---|---|---|
| 3,577,474 | 5/1971 | Jacobson | 260/668 |
| 3,579,596 | 5/1971 | Mullin et al. | 570/101 |
| 3,651,167 | 3/1972 | de Rosset | 260/681.5 |
| 3,691,102 | 9/1972 | Swift | 252/469 |
| 3,725,304 | 4/1973 | Wilhelm | 252/441 |
| 3,745,112 | 7/1973 | Rausch | 208/139 |
| 3,755,481 | 8/1973 | Hayes | 260/668 |
| 3,761,531 | 9/1973 | Bloch | 260/668 |
| 3,840,475 | 10/1974 | Davis | 252/441 |
| 3,855,347 | 12/1974 | Oricchio | 570/204 |
| 3,864,284 | 2/1975 | Clippinger et al. | 252/466 |
| 3,883,419 | 5/1975 | Itoh et al. | 208/138 |
| 3,892,683 | 7/1975 | Germanas et al. | 252/442 |
| 3,929,683 | 12/1975 | Antos | 252/466 |
| 3,943,071 | 3/1976 | Mitsche | 252/448 |
| 3,948,804 | 4/1976 | Rausch | 252/442 |
| 3,968,053 | 7/1976 | Rausch | 252/439 |
| 4,016,068 | 4/1977 | Rausch | 208/139 |
| 4,413,152 | 11/1983 | Arena | 568/863 |
| 4,511,673 | 4/1985 | Eto | 502/525 |
| 4,672,146 | 6/1987 | Abrevayz et al. | 585/560 |
| 4,716,143 | 12/1987 | Imai | 502/326 |
| 4,749,817 | 6/1988 | George et al. | 570/204 |
| 4,786,625 | 11/1988 | Imai et al. | 502/326 |

OTHER PUBLICATIONS

Lange, "Handbook of Chemistry", 10th ed., pp. 450 and 451 (1961).
C. J. Noelke et al., Platinum-Alumina with Special Treatments, 1979 American Chemical Society, pp. 325-328.

Primary Examiner—J. E. Evans

[57] ABSTRACT

A process for the hydrodechlorination of carbon tetrachloride to produce chloroform and methylene chloride utilizes a supported platinum catalyst that is subjected to chloride pre-treatment. The platinum catalyst may be promoted with small amounts of metals such as tin. By-product production is decreased and duration of catalyst activity is improved by the process of this invention.

15 Claims, No Drawings

VAPOR PHASE HYDROGENATION OF CARBON TETRACHLORIDE

BACKGROUND OF THE INVENTION

This invention is related to the vapor phase hydrogenation of carbon tetrachloride to form chloroform and methylene chloride.

Various methods of dehalogenating saturated and unsaturated organic compounds are known. For example, U.S. Pat. No. 3,579,596, issued to Mullin et al. on May 18, 1971, is directed to the vapor phase dechlorination of carbon tetrachloride and/or chloroform in the presence of a platinum catalyst. The hydrodechlorination of carbon tetrachloride with hydrogen over peripherally deposited platinum on alumina is also discussed by Weiss et al. in *Journal of Catalysis* 22, 245-254 (1971). However, as discussed by Noelke and Rase in *Ind. Eng. Chem. Prod. Res. Dev.* 18, 325-328 (1979), such processes have been marked with poor selectivity, rapidly declining catalyst activity and short reactor operating cycles. Various treatments have been explored to improve activity and selectivity. These include pretreating catalysts with sulfur and hydrogen.

A need remains for a process for hydrogenating carbon tetrachloride to form chloroform and methylene chloride that is selective to the desired products, results in minimal by-product formation and shows minimal decline in catalyst activity.

SUMMARY OF THE INVENTION

The present invention is a process for the catalytic hydrogenation of carbon tetrachloride to produce chloroform and methylene chloride comprising passing a reactant feed comprising carbon tetrachloride and hydrogen over a catalyst selected from the group consisting of (1) a supported platinum group metal catalyst subjected to a pretreatment comprising exposing the catalyst to a chloride source;

(2) a supported platinum group metal catalyst further comprising at least one component selected from tin. rhenium, germanium, titanium, lead, silicon, phosphorus, arsenic, antimony, bismuth or mixtures thereof; and (3) a supported platinum group metal catalyst further comprising at least one component selected from tin, rhenium, germanium, titanium, lead, silicon, phosphorus, arsenic, antimony, bismuth or mixtures thereof subjected to a pretreatment comprising exposing the catalyst to a chloride source under conditions sufficient to form chloroform and methylene chloride.

It is surprising that by the practice of this process production of by-products such as hexachloroethane, perchloroethylene and methane is significantly reduced; carbon tetrachloride conversion level is maintained relatively constant; and the rate of catalyst deactivation is low.

DETAILED DESCRIPTION OF THE ILLUSTRATIVE EMBODIMENTS

The present invention comprises a vapor phase process wherein carbon tetrachloride is contacted with hydrogen in the presence of a platinum group metal catalyst under reaction conditions sufficient to form chloroform and methylene chloride.

The carbon tetrachloride and hydrogen are contacted at any temperature and pressure at which the desired hydrodechlorination will occur. It is preferred that the temperature is at least about 50° C. and no greater than about 200° C.; more preferred that the temperature is at least about 75° C. and no greater than about 150° C.; and most preferred that the temperature is at least about 80° C. and no greater than about 130° C. The pressure is preferred to be at least about atmospheric and no greater than about 200 psig; more preferred that the pressure is about 15 psig and no greater than about 150 psig; and most preferred that the pressure is at least 25 psig and no greater than 100 psig. It will be recognized by one skilled in the art that higher temperatures and pressures are operable in the practice of this invention, but may not be preferred due to economic or other considerations. The process may be conducted in a batch or continuous manner.

Hydrogen and carbon tetrachloride are typically reacted to from chloroform and methylene chloride. In some preferred embodiments, hydrogen chloride is also included in the reactant feed. Any amounts of hydrogen, carbon tetrachloride and, optionally, hydrogen chloride which will result in the formation of chloroform and methylene chloride at an acceptable yield are useful in the practice of the present invention. Preferably the mole ratio of hydrogen to carbon tetrachloride ranges from about 1:1 to about 30:1: more preferably from about 2:1 to about 12:1 and even more preferably from about 3:1 to about 9:1. The mole ratio of carbon tetrachloride to hydrogen chloride ranges from about 1:0 to about 1:6; more preferably from about 1:1 to about 1:2. The upper limit on the amount of hydrogen chloride present in the reactant feed is related to catalyst activity. The activity of the catalyst, as determined by carbon tetrachloride conversion, appears to decrease as the amount of hydrogen chloride in the reactant feed increases. However, selectivity to chloroform increases as the amount of hydrogen chloride in the reactant feed increases. Thus, one skilled in the art will recognize that the optimum amount of hydrogen chloride to be included in the reactant feed will be selected to balance conversion of carbon tetrachloride and selectivity to chloroform. In reaction schemes wherein it is feasible to recycle significant amounts of carbon tetrachloride, the selectivity to chloroform obtained by higher amounts of hydrogen chloride may outweigh loss of conversion of carbon tetrachloride.

Catalysts useful in the practice of this invention are platinum group metal containing catalysts. By platinum group metal is meant ruthenium, rhodium. palladium, osmium, iridium, platinum and mixtures thereof. The catalyst of the present invention will preferably contain platinum. The catalyst, in certain preferred embodiments, will also contain a second metal component wherein the second metal comprises tin, titanium, germanium, rhenium, silicon, lead, phosphorus, arsenic, antimony, bismuth or mixtures thereof. It is preferred that the catalyst contain platinum and at least one of tin, titanium or germanium. It is more preferred that the catalyst contain platinum and tin.

The amount of platinum group metal present in the catalyst is preferably at least about 0.01 weight percent based on the weight of the total catalyst and no greater than about 5.0 weight percent. Preferred ranges are from about 0.03 weight percent to about 0.5 weight percent.

The second metal, when present, is preferably present in a weight ratio of platinum group metal to second metal of from about 500:1 to about 2:1 . The ratio is more preferably from about 200:1 to about 10:1.

The catalyst useful in the present invention is preferably supported. It is preferred that the support be a porous, adsorptive, high-surface area support having a surface area of about 25 to about 500 square meters per gram. Non-limiting examples of suitable support materials include activated carbon, coke or charcoal; silica or silica gel, silicon carbide, clays and silicates including those synthetically prepared and naturally occurring, which may or may not be acid treated, for example attapulgus clay, diatomaceous earth, fuller's earth, kaoline, kieselguhr, etc.; inorganic oxides such as alumina, titanium dioxide, zirconium dioxide, chromium oxide, zinc oxide, magnesia, thoria, boria, silica-alumina, silica-zirconia, silica-magnesia, chromia-alumina, etc.; crystalline zeolitic aluminosilicates; and combinations of one or more elements from one or more of these groups. It is preferred to use alumina supports for the catalysts of the present invention.

Preferred supports have surface areas ranging from about 50 to about 350 m$^2$/gm, more preferably from about 80 to about 250 m$^2$/gm. The average pore diameter of the preferred support ranges from about 25 to about 200 angstroms, more preferably from about 50 to about 125 angstroms. The average diameter of the catalyst is from about 1/16 to about ¼ inch.

The platinum group metal and second metal may be incorporated into the catalyst support in any suitable manner. Examples of suitable techniques include precipitation, ion-exchange or impregnation. The metals may be incorporated into the support at the same time or may be incorporated separately. In a preferred embodiment, the platinum group metal and second metals are incorporated separately.

The method of incorporation into the support is one variable which affects the distribution of the metal on the support. In the practice of the present invention, the platinum group metal may be distributed on the surface of the catalyst support or it may be distributed on or within the support. By distribution of the metal on or within the support, it is meant the distance from the surface of the support that the metal or metals penetrate measured in microns. It is preferred that the platinum group metal is distributed at least about 50 microns and no greater than about 650 microns from the surface and more preferred that it is distributed at least about 250 microns and no greater than about 350 microns from the surface.

Like the platinum group metal, the second metal may be located on the surface of the support or it may be distributed on or within the support. It is preferred that the second metal is distributed at least about 100 microns and no greater than about 100 microns from the surface. It is more preferred the second metal is distributed at least about 300 microns and no greater than about 500 microns from the surface.

In addition to the platinum group metal and the second metal, the catalyst may contain other components such as alkali metal, alkaline metal, halogen, sulfur and other known catalyst modifiers.

The catalysts useful in this invention may be purchased commercially. An example is a platinum on alumina catalyst. The catalysts may also be prepared by methods known in the art. For example. U.S. Pat. No. 4,786,625 to Imai et al., issued Nov. 22, 1988, describes a catalyst comprising a platinum group metal component, a modifier metal component selected from group consisting of tin, germanium, rhenium and mixtures thereof on a refractory oxide support having a nominal diameter of at least about 850 microns wherein the platinum group metal component is surface impregnated such that the average concentration of the surface-impregnated platinum group component on the outside 100 micron layer of the catalyst is at least 2 times the concentration of the platinum group component in the 200 micron diameter center core of the catalyst and wherein the modifier metal component is uniformly impregnated through the refractory oxide support and a method of making such a catalyst.

Prior to being used in the process of the present invention, the catalyst is preferably subjected to a pre-treatment comprising treatment with a chloride source. In one preferred embodiment, the catalyst is subjected to a multi-step pre-treatment comprising drying the catalyst, reducing the catalyst, and subjecting the catalyst to at least two treatments with a chloride source wherein a later treatment or treatments with the chloride source is conducted at a temperature lower than that used in an earlier treatment.

For example, in one preferred embodiment, the catalyst is subjected to a pre-treatment comprising the following steps:

(1) drying the catalyst under an diluent gas at an elevated temperature:

(2) treating the catalyst with a chloride source selected from the group comprising hydrochloric acid and chlorine at an elevated temperature:

(3) reducing the catalyst: and (4) treating the catalyst a second time with a chloride source selected from the group comprising hydrochloric acid and chlorine at a temperature less than the temperature used in step (2).

In the drying step, it is preferred that the diluent gas is nitrogen. The temperature is preferably in the range of from about 100° C. to about 500° C. The time required for the drying step is preferably in the range of from about two hours to about six hours.

In the first chloride treatment, the chloride source with which the catalyst is treated is preferably hydrochloric acid. The temperature in this step of the pre-treatment is preferably in the range of from about 150° C. to about 300° C. The time required for this step is preferably in the range of from about two hours to about four hours.

In the reduction, the catalyst is reduced using a conventional reducing agent. Examples of suitable reducing agents include hydrogen, hydrazine and formaldehyde. The reducing agent is preferably hydrogen. The temperature in this step of the pre-treatment is preferably in the range of from about 150° C. to about 500° C. The time required for this step is preferably in the range of from about two hours to about twenty-four hours. As will be recognized by one skilled in the art, preferred temperatures and times are related so that at higher temperatures, less time will be required and at lower temperatures, more time will be required. The catalyst is cooled after this step, preferably to a temperature in the range of from about 80° C. to about 150° C.

In the second chloriding treatment, the chloride source with which the catalyst is treated is preferably hydrochloric acid. The temperature in this step of the pre-treatment is preferably in the range of from about 80° C. to about 150° C., provided that the temperature used is less than that used in step (2). The time required for this step is preferably in the range of from about fifteen minutes to about two hours.

It will be recognized by one skilled in the art that the order of the various parts of the pre-treatment may be varied and in some cases steps will overlap. For example, the catalyst might be treated with a diluent gas and a chloride source at elevated temperatures simultaneously or the treatment with the inert gas and the chloride source may overlap for some period of time.

The following examples are provided to illustrate the invention and should not be interpreted as limiting it in any way. Unless stated otherwise, all parts and percentages are by weight.

EXAMPLE 1

Preparation of Titanium Promoted Catalyst

A 0.266 g portion of $H_2PtCl_6.3H_2O$ and 0.1180 g of $(NH_4)_2TiO(C_2O_2)_2$ are dissolved in the incipient wetness volume of 15.0 cc $1.0 \times 10^{-2}$ N HCl and added to 20 grams of alumina having a surface are of about 200 $m^2$/g. This produces a catalyst containing 0.5 weight percent platinum and 0.1 weight percent titanium. The catalyst is air dried at ambient temperature for 12 hours. The catalyst is then calcined in air at 400° C. for four hours. The calcined catalyst is then reduced in a mixture of 10 percent hydrogen in nitrogen starting at 25° C. and the temperature is raised to 400° C. at 10° C. per minute and held there for two hours. The catalyst is cooled under the reducing medium to 25° C. flushed with nitrogen and passivated by exposure to one percent oxygen in nitrogen.

EXAMPLE 2

Preparation of Tin Promoted Catalyst

The procedure outlined in Example 1 is followed with the exception that 0.0037 g of $SnCl_2.2H_2O$ is substituted for the $(NH_4)_2TiO(C_2O_2)_2$.

EXAMPLE 3

Sequential Impregnation

The procedure of Example 1 is followed to produce a tin promoted catalyst except that 0.037 gm $SnCl_2$ is dissolved in 15.0 cc 1.0 M HCl and added to 20.00 gm of alumina. The alumina is air dried at ambient temperature for 12 hours and calcined in air at 400° C. for four hours. The catalyst is cooled to room temperature and then impregnated with 0.266 gm of $H_2PtCl_6.3H_2O$ dissolved in 15.0 cc of $1.0 \times 10^{-2}$ M HCl solution. The drying, calcination and reduction procedures of Example 1 are then followed to produce the catalyst.

A phosphorus containing catalyst is prepared using phosphoric acid in the procedure described above.

A germanium containing catalyst is prepared as described above using a commercially obtained ICP (inductively coupled plasma) standard solution containing germanium.

EXAMPLE 4

Hydrogenation Reaction

A 0.5 inch by 12 inch Hastelloy C reactor tube fitted with a concentric thermal well is charged with 5.0 $cm^3$ (3.1 g) of a catalyst prepared in Example 1 (Runs 1–4). Example 2 (Runs 5–6) or Example 3 (Runs 7–9). The reactor is purged with $N_2$ and HCl at a 10:1 molar ratio and a total gas flow of 200 $cm^3$ per minute. The pressure is maintained at 30 psig by a research control valve. The reactor is heated to 100° C. and held for one hour. The reactor is temperature programmed to 200° C. and held for one hour. The HCl flow is stopped and the reactor is cooled to 100° C. under flowing $N_2$. The $N_2$ is replaced with $H_2$ and the reactor is temperature programmed at 10° C. per minute to 200° C. and held there for two hours. The reactor is cooled to 100° C. and the $H_2$ flow is set to 65 $cm^3$ per minute with a HCl flow of 2.5 $cm^3$ per minute. Vaporized $CCl_4$ is introduced at a liquid hourly space velocity (LHSV) of 0.5. Reaction products are monitored by on-line gas chromatography and the results are given in Table I below.

TABLE I

| Run | Pt (ppm) | Second Metal | Second Metal (F) (ppm)[1] | Second Metal (U) (ppm)[2] | $CH_4$ (%) | Pt Profile (microns) | Temp exo/base °C. | LHSV[3] |
|---|---|---|---|---|---|---|---|---|
| 1 | 4500 | Ti | 23 | — | 14.9 | 150 | 109.6/100 | 0.5 |
| 2 | 4600 | Ti | 120 | 75 | 9.7 | 300 | 110/100 | 0.5 |
| 3 | 4500 | Ti | 560 | 310 | 8.2 | 300 | 105.8/100 | 0.5 |
| 4 | 4600 | Ti | 980 | 440 | 8.6 | 300 | 112.5/110 | 0.25 |
| 5 | 4500 | Sn | 580 | 448 | 7.0 | 450 | 100/90 | 0.5 |
| 6 | 4600 | Sn | 850 | 627 | 6.84 | 550 | 102/90 | 0.5 |
| 7 | 5000 | Sn | 890 | 750 | 5.45 | 450 | 95.5/90 | 0.5 |
| 8 | 4940 | Ge | 750 | NA | 8.3 | 400 | 84.5/80 | 0.5 (92.0%) |
| 9 | 4600 | P | 150 | NA | 9.01 | 350 | 106/100 | 0.5 (99.1%) |

[1] Content of Second Metal in Fresh catalyst
[2] Content of Second Metal in Used catalyst
[3] All conversions are 100% unless noted In the following examples, a computer controlled apparatus constructed of a corrosion resistant nickel/copper alloy is used. The apparatus comprises two gas lines with one being fed by a cylinder of high purity hydrogen and the other being fed by a cylinder of electronic grade hydrogen chloride. Both are flow controlled by mass flow controllers to a common packed sample cylinder where the gasses are mixed and heated to 120° C. by resistive heating. A high pressure syringe pump is used to meter carbon tetrachloride ($CCl_4$) to another packed sample cylinder where it is vaporized and superheated to about 105° C. by resistive heating. The two gas streams are mixed and fed to a reactor packed with 5 cubic centimeters of a commercially available catalyst (0.3 percent platinum on alumina). After passing over the catalyst, the effluent is transferred through a heated exit line to a gas sampling valve which injects a sample for gas chromatographic analysis. The bulk of the reactor effluent is then passed through a cold trap and then to a vent.

COMPARATIVE EXAMPLE C-1

The process outlined above is followed. The catalyst is pre-treated by nitrogen drying at a temperature of about 200° C. with a nitrogen flow of about 100 cm³/min for about two hours. The catalyst is then reduced by treatment with hydrogen at 200° C. for about two hours before the reactant feed is started. The conversion of carbon tetrachloride and the ratio of methane to ethane are measured over time. The conversion of carbon tetrachloride is initially nearly 100 percent and then drops to about 20 percent in about three hours and then gradually increases to about 85 percent after about 20 hours of run time. After fifty hours of run time, the conversion has increased to over 90 percent. The methane to ethane ratio is near 100:1 at the beginning of the run time; drops to about 8:1 after about two hours of run time; and then increases gradually to about 60:1. The methane to ethane ratio is related to catalyst deactivation with a higher ratio corresponding to a lower rate of deactivation. The primary products of this reaction are chloroform and methane. During the period of low carbon tetrachloride conversion, perchloroethylene and hexachlorethane are produced in significant quantities as identified by gas chromatography.

COMPARATIVE EXAMPLE C-2

The general process and pre-treatment outlined in Example C-1 is followed with the exception that a 6:1 molar ratio of hydrogen to hydrogen chloride at 100° C. is passed over the catalyst after it is dried and reduced. Following the treatment with hydrogen chloride, the catalyst is treated with pure hydrogen for thirty minutes at 100° C. before the carbon tetrachloride flow is begun. The conversion of carbon tetrachloride starts out near 100 percent and drops to less than 10 percent within minutes of beginning the run and then gradually increases to about 90 percent after 200 hours of run time. The methane to ethane ratio reaches only about 30:1 in this experiment.

EXAMPLE 5

Effect of Chloride Soak

In this example, the catalyst is dried and then reduced with hydrogen as described in Example C-1. The catalyst is then exposed to pure hydrogen chloride at 100° C. for one hour. Next a mixture of hydrogen chloride and hydrogen in a 1:1 molar ratio is passed over the catalyst for about 30 minutes at a temperature of about 100° C. Then carbon tetrachloride is added to the feed so that the molar ratio of hydrogen to carbon tetrachloride to hydrogen chloride is about 6:1:6. After about 15 minutes, the amount of hydrogen chloride is reduced so that the molar ratio of hydrogen to carbon tetrachloride to hydrogen chloride is about 6:1:1. The carbon tetrachloride conversion is relatively constant at about 98 percent. No drop in conversion is observed. No perchloroethylene or hexachloroethane are detected. The methane to ethane ratio quickly climbs to about 80:1 and lines out at about 100:1 to about 120:1. The rate of catalyst deactivation is about one percent loss of conversion per 300 hours of operation.

EXAMPLE 6

Temperature Hydrogen Chloride Treatment

In this example, the catalyst is dried under nitrogen at 200° C. for four hours. It is then cooled to 100° C. and pure hydrogen chloride is passed over the catalyst as the temperature is increased to 200° C. and held there for two hours. The gas is then changed from pure hydrogen chloride to pure hydrogen and the temperature is maintained at 200° C. for two hours. Next a mixture of hydrogen chloride and hydrogen in a 1:1 molar ratio is passed over the catalyst for about 30 minutes at a temperature of about 100° C. Then carbon tetrachloride is added to the feed so that the molar ratio of hydrogen to carbon tetrachloride to hydrogen chloride is about 6:1:6. After about 15 minutes, the amount of hydrogen chloride is reduced so that the molar ratio of hydrogen to carbon tetrachloride to hydrogen chloride is about 6:1:1. The conversion of carbon tetrachloride over time is about 99.8 percent. A comparison of Examples 5 and 6 shows that treatment with hydrogen chloride at a high temperature (200° C.) followed by a chloride soak at a lower temperature (100° C.) results in a higher carbon tetrachloride conversion. The methane to ethane ratio ranges from about 120:1 to 180:1. The rate of deactivation is estimated at about 1 percent conversion loss per 2000 hours of operation.

EXAMPLE 7

Reduction of Methane Production

The procedure of Example 5 is followed with the exception that the amount of hydrogen chloride in the reactant feed was varied from a ratio of 6:1:0 to 6:1:1 to 6:1:6, $H_2:CCl_4:HCl$. The conversion of carbon tetrachloride dropped from about 98.5 percent when the ratio is 6:1:0 to about 90.5 percent when the ratio 6:1:6. The selectivity to methane decreased from about 25.5 percent when the ratio is 6:1:0 to about 20.75 when the ratio is 6:1:6. A lower selectivity to methane indicates a higher selectivity to chloroform.

What is claimed is:

1. A process for the catalytic hydrogenation of carbon tetrachloride to produce chloroform and methylene chloride comprising passing a reactant feed comprising carbon tetrachloride, hydrogen chloride and hydrogen over a catalyst selected from the group consisting of
   (1) a supported platinum group metal catalyst subjected to a pretreatment comprising exposing the catalyst to a chloride source prior to contacting the reactant feed with the catalyst;
   (2) a supported platinum group metal catalyst further comprising at least one component selected from tin, rhenium, germanium, titanium, lead, silicon, phosphorus, arsenic, antimony, bismuth or mixtures thereof; and
   (3) a supported platinum group metal catalyst further comprising at least one component selected from tin, rhenium, germanium, titanium, lead, silicon, phosphorus, arsenic, antimony, bismuth or mixtures thereof subjected to a pretreatment comprising exposing the catalyst to a chloride source prior to contacting the reactant feed with the catalyst
under conditions sufficient to form chloroform and methylene chloride.

2. The process of claim 1 wherein the catalyst is a supported platinum group metal catalyst subjected to a pretreatment comprising exposing the catalyst to a chloride source.

3. The process of claim 2 wherein the platinum group metal is platinum.

4. The process of claim 1 wherein the catalyst is a supported platinum group metal catalyst further comprising at least one component selected from tin, rhenium, geranium, titanium, lead, silicon, phosphorus, arsenic, antimony, bismuth or mixtures thereof.

5. The process of claim 4 wherein the platinum group metal is platinum.

6. The process of claim 1 wherein the chloride source is hydrochloric acid.

7. The process of claim 1 wherein the reaction is conducted at a temperature range between about 50° C. and 200° C.

8. The process of claim 1 wherein the catalyst is a supported platinum group metal catalyst further comprising at least one component selected from tin, titanium and geranium and mixtures thereof.

9. The process of claim 8 wherein the component is titanium.

10. A process for the catalytic hydrogenation of carbon tetrachloride to produce chloroform and methylene chloride comprising passing a reactant feed comprising carbon tetrachloride and hydrogen over a supported platinum catalyst further comprising tin under conditions sufficient to form chloroform and methylene chloride.

11. The process of claim 10 wherein the platinum is distributed on the support between about 50 and 650 microns from the surface and the tin is distributed between about 100 and 1000 microns from the surface.

12. The process of claim 11 wherein the platinum is distributed on the support between about 250 and 350 microns from the surface and the tin is distributed between about 300 and 500 microns from the surface.

13. A process for the catalytic hydrogenation of carbon tetrachloride to produce chloroform and methylene chloride comprising passing a reactant feed comprising carbon tetrachloride and hydrogen over a catalyst selected from the group consisting of
  (1) a supported platinum group metal catalyst subjected to a pretreatment comprising exposing the catalyst to a chloride source wherein the pretreatment comprises at least two sequential treatments with a chloride source wherein a later treatment is conducted at a temperature lower than that used in an earlier treatment; and
  (2) a supported platinum group metal catalyst further comprising at least one component selected from tin, rhenium, germanium, titanium, lead, silicon, phosphorus, arsenic, antimony, bismuth or mixtures thereof subjected to a pretreatment comprising exposing the catalyst to a chloride source wherein a later treatment is conducted at a temperature lower than that used in an earlier treatment
under conditions sufficient to form chloroform and methylene chloride.

14. The process of claim 13 wherein the pretreatment of the catalyst comprises:
  (1) drying the catalyst under an diluent gas at an elevated temperature;
  (2) treating the catalyst with a chloride source selected from the group comprising hydrochloric acid and chlorine at an elevated temperature;
  (3) reducing the catalyst; and
  (4) treating the catalyst a second time with a chloride source selected from the group comprising hydrochloric acid and chlorine at a temperature less than the temperature used in step (2).

15. A process for the vapor phase catalytic hydrogenation of carbon tetrachloride to produce chloroform and methylene chloride comprising passing a reactant feed comprising carbon tetrachloride and hydrogen over a supported platinum group metal catalyst further comprising tin.

* * * * *